United States Patent [19]
Neumeier

[11] 3,964,485
[45] June 22, 1976

[54] ENTEROSTOMY APPLIANCES
[75] Inventor: Erich Neumeier, Mosinee, Wis.
[73] Assignee: Marsan Manufacturing Company, Inc., Wausau, Wis.
[22] Filed: Sept. 20, 1974
[21] Appl. No.: 507,734

[52] U.S. Cl. ............................................. 128/283
[51] Int. Cl.² ........................................... A61F 5/44
[58] Field of Search ................................... 128/283

[56] References Cited
UNITED STATES PATENTS

| | | | |
|---|---|---|---|
| 2,818,069 | 12/1957 | Fenton | 128/283 |
| 2,874,697 | 2/1959 | Johnson | 128/283 |
| 3,076,458 | 2/1963 | Mason | 128/283 |
| 3,528,420 | 9/1970 | Neilsen | 128/283 |
| 3,762,412 | 10/1973 | Frank | 128/283 |

Primary Examiner—Richard A. Gaudet
Assistant Examiner—Henry S. Layton
Attorney, Agent, or Firm—Merriam, Marshall, Shapiro & Klose

[57] ABSTRACT

Disclosed are enterostomy appliance assemblies employing a collection pouch element, a flexible sealing band element and an abdominal wall-contacting gasket element including an apertured gasket back wall portion which is relatively convex and flexible and a gasket front wall surface which is relatively planar and rigid and which is provided with a relatively rigid outwardly-extending frustoconical flange member. The flange member and the gasket front wall portion establish a continuous groove with two adjacent sealing surfaces at acute angles to each other for fluid-tight attachment of the pouch to the gasket with the sealing band.

6 Claims, 4 Drawing Figures

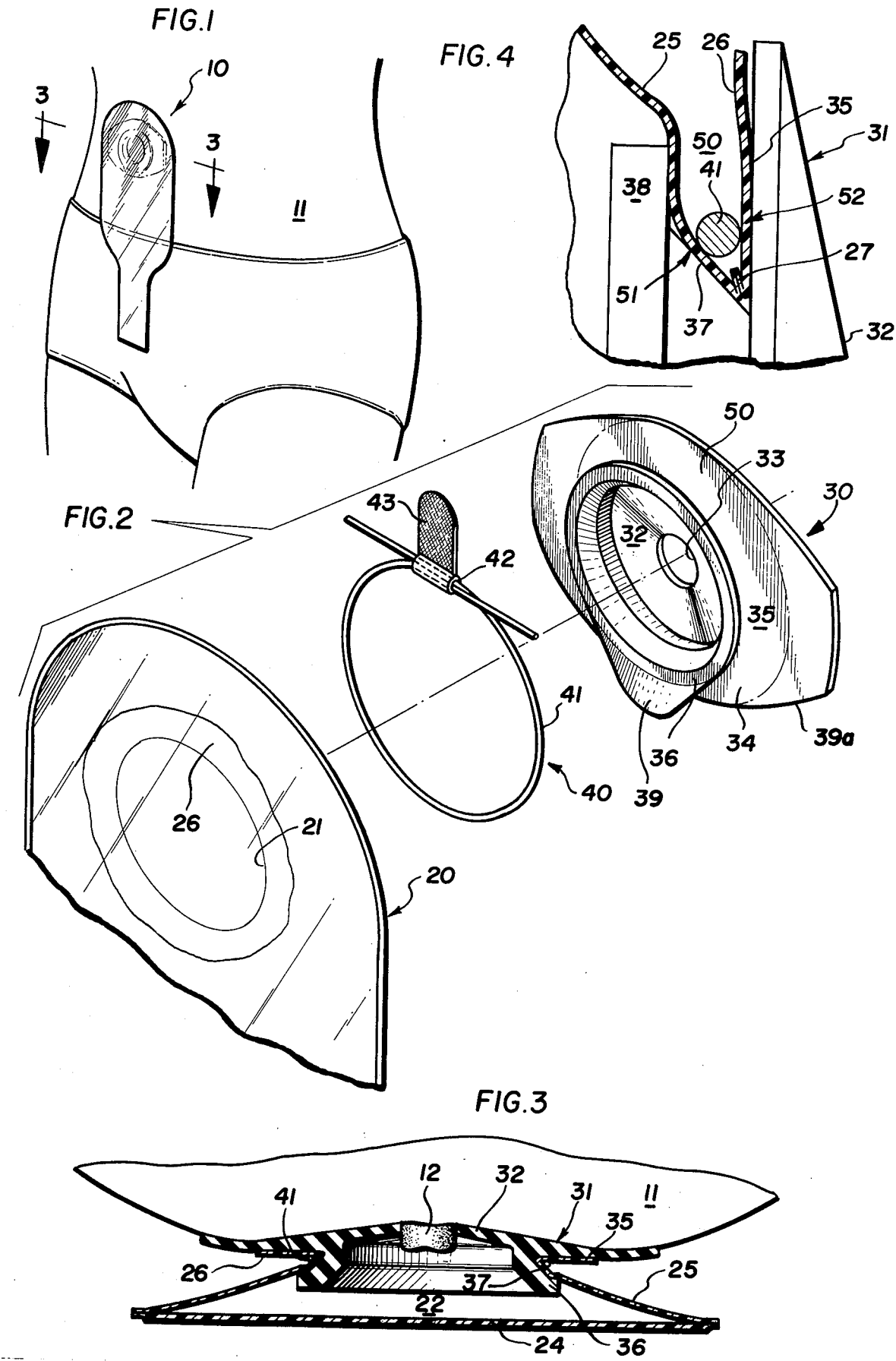

ENTEROSTOMY APPLIANCES

BACKGROUND OF THE INVENTION

The present invention relates generally to enterostomy appliances for use in the collection of solid and/or liquid waste materials at the site of a surgically-developed abdominal fistula and more particularly to improved appliances constructed to permit a comfortable, liquid-tight, odor-proof sealing relation between the stoma and surrounding abdominal wall of the wearer and the interior of a waste material collection pouch, drain, bag or the like.

Among the principal goals in the fabrication of ostomy drainage apparatus are the development of appliances of the simplest construction, with the fewest possible number of parts, which yet provide for comfortable attachment of a collection pouch at the ostomy site, for a fluid-tight seal between the abdomen of the wearer and the interior of the collection pouch, and for easy removal and replacement of the collection pouch. To this end many devices have been developed in the prior art. To varying degrees, it has been found achievement of one goal has been at the expense of the achievement of another.

U.S. Pat. No. 3,074,404, for example, relates to gasketed devices designed to provide an improved fluid-tight seal with the wearer's abdomen, but which necessarily include a rigid plastic bulbous gasket element which may be less than comfortable for the wearer. U.S. Pat. No. 3,495,592 relates to proposed tightly sealing gasket devices which would include an apparently comfortably-fitting flexible element but which also must incorporate a separately constructed and assembled rigidifying member. U.S. Pat. Nos. 3,481,336 and 3,283,757 relate to devices which are said to facilitate easy removal and replacement of collection bags but which must incorporate a pair of rather complicated interlocking rings to effect an adequate seal. In sum, none of the gasketed devices or complete assemblies of the prior art has exhibited all the desirable aspects of simplicity of construction and use, flexibility for comfort and better sealing to the abdomen, as well as sufficient rigidity for better support, sealing, and easy removal and replacement of collection pouches.

BRIEF SUMMARY OF THE INVENTION

Proposed ostomy appliances and assemblies provided by the present invention incorporate the use of a collection pouch element, a flexible and preferably adjustable sealing band element, and a novel, easily-fabricated gasket element. The gasket element is provided with an apertured relatively convex and flexible back wall portion which in use comfortably and securely abuts the wearer's abdomen about the stoma. The front wall of the gasket element includes a relatively planar and rigid surface and is provided with an outwardly extending frusto-conical flange member facilitating access to the interior of the collection bag supported by the flange. The surface of the planar gasket front wall and the exterior surface of the frusto-conical flange member together generate a groove having acutely angled, adjacent sealing surfaces at which the collection bag may be releasably secured to the gasket element in fluid-tight relation by means of the flexible sealing band.

Preferred embodiments may include a specialized lip element on the frusto-conical member for facilitating placement of the collection bags.

These and other aspects and advantages of the present invention will be understood from the following detailed description of presently preferred embodiments, considered in connection with the drawing wherein:

FIG. 1 is a front elevation of an assembly according to the teachings of the invention in position on a wearer;

FIG. 2 is an exploded view of an assembly as in FIG. 1;

FIG. 3 is a sectional view taken along lines 3—3 of FIG. 1; and

FIG. 4 is a fragmentary view illustrating the cooperative relation of a collection pouch, sealing band and gasket element in the use according to the teachings of the invention.

DETAILED DESCRIPTION

Referring to FIGS. 1 and 3, and enterostomy appliance assembly 10 according to the invention is shown in place at the abdominal surface 11 of the wearer, accommodating stoma 12 for collection of solid and liquid wastes therefrom. The principal elements of assembly 10 include a collection pouch element 20, a gasket element 30 and a sealing band element 40.

Pouch element 20 may be fabricated of any standard material, i.e., it may be made of any suitable plastic, rubber, or other film material which is preferably impermeable to the liquid and/or gaseous materials generated at the stoma. Pouch element 20 may similarly be of standard configuration form, i.e., it may be in the form of permanent or disposable type usually referred to as a pouch, drain, bag, bladder or the like. The only generally necessary elements of pouch 20 are an opening 21 into the relatively enclosed collection space 22 and sufficient pouch material available at opening 20 to permit proper mounting in sealed relation to gasket element 30. In the preferred embodiment illustrated, pouch 20 is in the form of tapered-bottom drain having front and back walls, 24, 25 respectively. Opening 21 in back wall 25 thereof is generally circular. For ease of attachment to gasket element 30, annular flange element 26 is provided about opening 21, preferably through use of a heat sealed joint 27 along the perimeter of opening 21.

Preferred structural aspects of gasket element 30 are shown in FIGS. 2, 3, and 4. As illustrated, the operative back wall 31 of gasket element 30 includes a convex portion 32 of a relatively flexible material such as chemically inactive rubber or vinyl plastic, which is preferably formed as a thinned portion of material constituting a unitary molded gasket element. In use, convex portion 32 comfortably abuts the oppositely convex abdomen 11 of the wearer with stoma 12 passing through the centrally-disposed oriface 33 in the convex portion. Operative gasket front wall 34 is seen to include a substantially planar surface 35 having an outwardly extending frusto-conical element 36. Element 36 has an outer surface 37 disposed to extend outwardly at an acute angle relative to surface 35. In the embodiment illustrated, frusto-conical element 36 is generally concentrically oriented with oriface 33 and has a circular cross-section. It is anticipated that element 36 may in some embodiments have an elliptical cross section and/or may simply be axially aligned (i.e., have an axis parallel to, though not necessarily coincident) with the axis of oriface 33. Frusto-conical element 36 preferably includes circumferential rim portion 38 extending outwardly in a plane generally parallel to the plane of gasket front wall surface 35. Rim 38 functions to maintain the structural integrity of element 36 allowing it to perform an enhanced supportive function with respect to a pouch. Also shown is a parabolically-shaped lip element 39 which extends operatively downwardly from rim 38 and generally further outwardly and away from gasket front wall 34.

A band element for use according to the invention may be of any suitable flexible, moderately elastic material and may take the form of one or more rubber bands, an O-ring or the like. Preferred construction of band element 40 includes providing an elastic strand 41, of fabric-coated rubber construction and rounded cross-section, the opposite ends of which are passed through tubular element 42 which is preferably constructed of moderately flexible plastic material. Tab element 43 is affixed to tube 42.

In operation, gasket element 30 is positioned at the abdomen 11 of the wearer by any suitable means including surgical cement, belts, and the like. When a belt is employed, ear-like flanges 39a, 39a may be provided on gasket element 30 and may include means (not shown) such as slots or hubs to accommodate attachment to the belt. In position, stoma 12 will pass through gasket oriface 33 and convex gasket back portion 32 will flexibly, and hence comfortably, abut abdomen 11 to provide a seal against leakage of waste material to the abdominal skin surrounding the stoma.

With gasket element 30 in place, pouch element 20 may be positioned and thereafter secured in place by means of band element 40. This process involves registering the edge of opening 21 of pouch element 20 in the continuous groove 50 formed at the joining of gasket planar surface 35 and over surface 37 of frusto-conical element 36 with bag flange element 26 adjacent surface 35 and pouch back wall 25 adjacent surface 37. Note that opening 21 is preferably dimensioned to be larger than the corresponding dimension of the innermost aspect of groove 50 but smaller than the outermost aspect of frusto-conical element 36.

With pouch element 20 in place on gasket element 30, band element 40 is registered with a strand 41 seated in groove 50. In position, strand 41 will urge flange 26 into intimate sealing contact with surface 35 at point 52 and bag back wall 25 into similar contact with surface 37 at point 51 to provide an exceptionally liquid-tight double sealing arrangement.

Mounting of bag element 20 on gasket element 40 is facilitated in the preferred embodiment by provision of lip 38 which serves as a starting point for slipping of the edge of opening 21 into groove 50 about frusto-conical element 35. This is especially advantageous when bag element 20 is of relatively inelastic material and consequently opening 21 has a relatively fixed diameter only slightly larger than the diameter of groove 50. Another obvious advantage of providing outwardly projecting lip element 39 is that it functions to prevent accidental temporary sealing-off of the opening of frusto-conical element 36 by the front wall 24 of the bag element through collapse against rim 38.

Positioning of band element 40 is facilitated in the preferred embodiment through provision of tube element 42 which permits easy alteration and adjustment of the band diameter, and thus easy alteration of the holding tension of the band, by a process of sliding strand 41 within tube 42 which is dimensioned to slideably grip two segments of the strand. Use of a strand of fabric-coated rubber enhances the sliding process because cloth surfaces of adjacent strand segments will functionally inhibit relative movement within tube 42 until sufficient pulling forces are applied to reduce the diameter of the rubber portion. Positioning is also facilitated by provision of tab element 43 which allows the users to easily grasp the band during mounting and removal of bag element 20.

The gasket element of the present invention is preferably formed as a generally unitary molded article sequentially molded of materials of differing hardnesses as such a process greatly facilitates formation of the convex flexible back wall portion and planar rigid front wall portion. It has been found, for example, that a suitable gasket according to the invention may be molded of neoprene or butyl rubber. Using such materials a preferred gasket would have a convex back wall portion formed of material with a durometer scale hardness (Shore, A scale) of about 30 to 40, and preferably about 35. Such construction allows for comfortable flexibility of the back wall portion. Structural rigidity of the planar front wall portion and the frusto-conical element is provided through use of materials with a durometer scale hardness of 55 to 65, and preferably about 60. Such structural rigidity of these elements is most desirable both for the purpose of providing firm surfaces for the sealing of the bag to the gasket and for providing ample support for the increasing weight of the bag as it is filled.

Obviously, modifications and variations of the above-described invention may be made without departing from the spirit and scope thereof. Therefore, only such limitations as are indicated by the appended claims should be placed thereon.

What is claimed is:

1. In an ostomy appliance assembly including a gasket element, a waste material collection pouch and flexible band means for releasably securing the collection pouch in sealed relation with the gasket element and wherein the gasket element includes a gasket body having operative front and back walls, the operative front wall including an outwardly-extending flange means for attachment and support of the collection pouch and the operative back wall including an outwardly-extending convex portion with a centrally disposed stoma-accommodating opening therein, an improvement in the gasket element comprising:

a gasket front wall and flange means composed of a material having a hardness greater than that of the material of which said back wall convex portion is composed, said convex portion consequently being relatively more flexible than said front wall and flange means, and wherein the surface of said gasket body front wall adjacent said flange means is substantially planar and said flange means is frusto-conical in shape, having an outer surface forming an acutely angled circumferential groove with said gasket body planar front wall surface.

2. The improvement of claim 1 wherein said convex portion of said gasket back wall is composed of a material having a durometer scale hardness of from 30 to 40.

3. The improvement of claim 2 wherein said convex portion material durometer scale hardness is 35.

4. The improvement of claim 1 wherein said front wall and flange means material durometer scale hardness is from 55 to 65.

5. The improvement of claim 4 wherein said front wall and flange means material durometer scale hardness is 60.

6. In an ostomy appliance assembly including a gasket element, a waste material collection pouch and flexible band means for releasably securing the collection pouch in sealed relation with the gasket element and wherein the gasket element includes a gasket body having operative front and back walls, the operative front wall including an outwardly-extending flange means for attachment and support of the collection pouch and the operative back wall including an outwardly-extending convex portion with a centrally disposed stoma-accommodating opening therein, an improvement in the gasket element comprising:

a substantially planar surface on said gasket front wall adjacent said flange means; and a gasket flange means frusto-conical in shape, having an outer surface forming an acutely angled circumferential groove with said planar surface.

\* \* \* \* \*